United States Patent [19]

Smith

[11] 4,002,672
[45] Jan. 11, 1977

[54] PROCESS FOR PRODUCING N-PHOSPHONOMETHYL GLYCINE

[75] Inventor: Lowell R. Smith, Chesterfield, Mo.

[73] Assignee: Monsanto Company, St. Louis, Mo.

[22] Filed: Mar. 22, 1972

[21] Appl. No.: 236,769

[52] U.S. Cl. .................. 260/502.5; 71/86; 260/535 R; 260/539 A; 260/606

[51] Int. Cl.² ............................ C07F 9/38

[58] Field of Search ................. 260/502.5

[56] References Cited

UNITED STATES PATENTS

| | | | |
|---|---|---|---|
| 3,134,800 | 5/1964 | Kagan et al. | 260/502.5 |
| 3,288,846 | 11/1966 | Irani et al. | 260/502.5 |
| 3,455,675 | 7/1969 | Irani | 260/502.5 |

*Primary Examiner*—Joseph E. Evans
*Attorney, Agent, or Firm*—William T. Black; Donald W. Peterson

[57] ABSTRACT

N-phosphonomethyl glycine is produced by the strong acid catalyzed hydrolysis of N-(phosphonomethyl) imino-diacetic acid. N-phosphonomethyl glycine is useful as a post-emergent herbicide.

14 Claims, No Drawings

PROCESS FOR PRODUCING N-PHOSPHONOMETHYL GLYCINE

This invention relates to a method of producing N-phosphonomethyl glycine and the salts thereof by the acid catalyzed hydrolysis of N-(phosphonomethyl) imino-diacetic acid. More particularly, this invention relates to the N-phosphonomethyl of N-Phosphonomethyl glycine and the salts thereof by the decomposition of N-(phosphonomethyl) imino-diacetic acid in a strong acid, the acid having a pKa of less than 2.2, preferably less than 1.5.

In accordance with the process of this invention, N-(phosphonomethyl) imino-diacetic acid

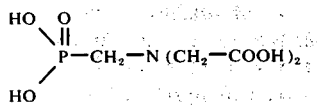

is contacted with a strong acid having a pKa of less than 2.2, at an elevated temperature so as to cause the decomposition or hydrolysis of the imino-diacetic acid into N-phosphonomethyl glycine and other decomposition products. The reaction mixture is then diluted with water and a water miscible organic solvent to precipitate N-phosphonomethyl glycine.

The manner of contacting the N-phosphonomethyl-imino-diacetic acid with the strong acid is not critical and can be accomplished in many ways. For example, one can form an admixture of the reactants and heat the mixture to the temperature of reaction in a suitable vessel. The N-phosphonomethyl-imino-diacetic acid can be added to the strong acid which has been preheated to the reaction temperature. A hot tube type reactor can also be employed in the process of this invention.

It is believed that the reaction takes place in accordance with the following equation:

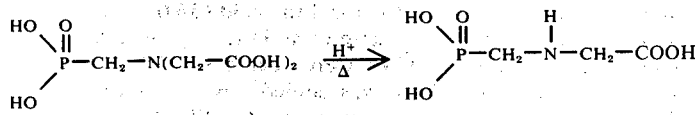

HCHO + HOCH$_2$—COOH + other decomposition products.

In conducting the process of this invention, the temperature of reaction can range from as low as 70° to 200° C. or even higher. It is preferred for ease of reaction and to obtain the best yield of product to conduct the process of this invention from about 80° to about 150° C.

The time of reaction is not narrowly critical and can vary from as low as one minute contact time to as high as 40 or more hours. Of course, it is obvious to those skilled in the art that the yield of product will vary with the reaction time and the temperature of the reaction. For example, shorter reaction times can be employed when the higher reaction temperatures are employed and longer reaction times will be employed at the lower range of temperature.

The ratio of the strong acid to the N-phosphonomethyl-imino-diacetic acid is not narrowly critical and can range from one part by weight N-phosphonomethyl-imino-diacetic acid to 100 parts by weight acid to 3 parts N-phosphonomethyl-imino-diacetic acid to one part acid. However, for ease of reaction and recovery and economics, it is preferred to employ N-phosphonomethyl-imino-diacetic acid in amounts of from one part by weight to 3 parts by weight of the strong acid.

The strong acids that can be employed in the process of this invention are those having a pKa of less than 2.2. It is preferred to employ in the process of this invention acids having a pKa of 1.5 or less. It is even more preferred to employ those acids having a pka of 1.0 or less. The strong acids useful in this invention include, for example, sulfuric acid, fuming sulfuric, hydrobromic, hydrochloric, hydroiodic, phosphoric, trifluoroacetic, dichloroacetic, iodic, sulfonic acid, phosphorous, sulfurous, chlorosulfonic, trichloroacetic, pyrophosphoric, sulfur trioxide and the like.

When sulfuric acid is employed as the strong acid in the process of this invention, the concentration can range from as low as 60% sulfuric acid to 20% fuming sulfuric acid, or even sulfur trioxide. It is preferred for best results to employ 5% fuming sulfuric acid.

The process of the instant invention is usually conducted at atmospheric pressure for ease of reaction and economics. Higher and lower pressures can be employed.

The starting N-phosphonomethyl-imino-diacetic acid starting material can be prepared by methods known in the art. For example, this material can be produced by the reaction of formaldehyde, iminodiacetic acid hydrochloride, and ortho-phosphorous acid in the presence of hydrochloric acid. The N-phosphonomethyl-imino-diacetic acid mixture resulting from this reaction can be employed per se in the process of this invention or the N-phosphonomethyl-imino-diacetic acid can be isolated and then employed in the process of this invention.

The organic solvent which is employed in the isolation of the product of this invention is one of the water miscible organic solvents and may include alcohols such as, methanol, ethanol, isopropanol, butanol and the like, dioxane, and other water soluble heterocyclics; carboxylic acids such as acetic acid, propionic acid and the like; ketones such as acetone, methylethyl ketone and the like; glycols and polyglycols, for example, ethylene glycol, propylene glycol, diethylene glycol, methyl cellosolve, dimethyl cellosolve, glycerol and the like. Many other water miscible organic solvents that can be employed in isolating the product of this invention will be apparent to those skilled in the art.

The compounds produced by the process of this invention are useful as herbicides.

The following examples serve to further illustrate the invention. All parts are parts by weight unless otherwise expressly set forth.

EXAMPLE 1

To a suitable reaction vessel was added 150 grams of 5% fuming sulfuric acid and the sulfuric acid heated to 90° C. To the fuming sulfuric acid was added over a one hour period 70 grams of N-(phosphonomethyl) imino-diacetic acid. The reaction mixture was heated at 100° C. for 2 hours at which time a nuclear magnetic resonance spectra indicated that no N-(phosphonomethyl) imino-diacetic acid starting material was present. Water (200 mls.) was added at a temperature of approximately 50° C. and then the reaction mixture vacuum distilled to 100° C. at 17 to 18 inches of mercury. The reaction mixture was then cooled to 30° C. and 375 mls. of 80% isopropanol was added. The isopropanol mixture was then chilled for 2 hours and filtered and the filter cake was washed with 80% isopropanol and 50 mls. of water and dried, yielding 35 grams of N-phosphonomethyl glycine of 93.5% purity. The filtrates and wash were combined and then stripped to 105° C. at 17 to 18 inches of mercury. The stripped material was cooled to 40° C. and 50% sodium hydroxide (235 grams) was added to the mixture to bring the pH to 2.45 at less than 60° C. This mixture was then distilled at atmospheric pressure to 105° C. The residue was cooled to 50° C. and methanol (200 mls.) was added and then the mixture was cooled to 10° C. The cooled mixture was stirred for one hour, filtered and the filter cake was washed with an additional 50 mls. of methanol. The residue was slurried in methanol (200 mls.), cooled to 15° C. and isopropylamine (7.0 grams) was added. This mixture was stirred for ½ hour, filtered and the residue was washed with methanol (100 mls.). The methanolic filtrates were combined and methanol was distilled off to a temperature of 70° C. To the residue was added 40 mls. of water and the residual methanol was then removed under vacuum until the pot residue temperature reached 75° C. There was obtained from this residue an additional 38 grams of N-phosphonomethyl glycine as an isopropylamine, salt solution having an assay of 33.8% N-phosphonomethyl glycine.

EXAMPLE 2

Sulfuric acid (30.0 grams, 98%) was charged into a suitable reaction vessel and heated to 100° C. N-phosphonomethyl imino-diacetic acid (22.8 grams) was added over a 1.5 hour period while maintaining the temperature at 100° to 110° C. The resultant mixture was heated at 110° to 115° C. for 15 minutes, diluted with approximately 50 ml. of water, cooled and a solution of 24 grams of sodium hydroxide and 50 ml. of water added to render the pH of 2.2. The mixture was evaporated at 110° C. under a vacuum to yield a semi-solid. Methanol (50 ml.) was added and the resultant mixture filtered and the filter cake was washed with an additional 25 ml. of methanol. The solid was dried at 100° C. to yield 57 grams of a material which assayed at 22.5% N-phosphonomethyl glycine.

EXAMPLE 3

To a suitable reaction vessel was charged 150 grams of 5% fuming sulfuric acid and the acid heated to 110° C. There was then added to the heated acid N-phosphonomethyl-imino-diacetic acid (50 grams) over a 1 hour period while maintaining the temperature at 110° C. The mixture was then heated an additional ½ hour at 110° C. At this point, a small sample placed in the nuclear magnetic resonance spectra device showed that none of the phosphonomethyl-imino-diacetic acid starting material remained. A portion of this reaction mixture weighing 167 grams was taken and 200 ml. of water added, while maintaining the temperature at below 30° C. The resultant mixture was steamed at 17 inches of mercury and up to a temperature of 100° C. To this reaction mixture was added 300 ml. of isopropanol and the mixture chilled. Water (50 ml.) was added and the mixture filtered and the residue dried to yield 21.0 grams of a material having a 92% assay for N-phosphonomethyl glycine.

The above isopropanol filtrate was stripped to 105° C. To the resultant residue was added 200 grams of sodium hydroxide as a 50% solution in water to adjust the pH to 2.5. The mixture was then stripped to 105° C., 200 grams of methanol added, chilled and filtered. The filter cake was washed with methanol and added to a mixture of 200 ml. of methanol and 4.0 grams of isopropylamine. The slurry was filtered and the methanolic filtrate was distilled to give 14.0 grams of a residue which was dissolved in 14.5 grams of water. This gave 28.5 grams of a solution containing 30.0% N-phosphonomethyl glycine.

EXAMPLE 4

To a suitable reaction vessel was added 150 grams of 98% sulfuric acid. The sulfuric acid was heated to 90° C., and N-phosphonomethyl-imino-diacetic acid (75 grams) added over a 1 hour period. The mixture was heated at 100° C. for an additional 2 hours. This gave 220.5 grams of a solution which analyzed 22.36% by weight N-phosphonomethyl glycine by ultraviolet absorption spectra.

EXAMPLE 5

Fuming sulfuric acid (5%, 150 grams) was added to a glass reaction vessel fitted with a stirrer and thermometer. The fuming sulfuric acid was heated to 110° C. and N-phosphonomethyl-imino-diacetic acid (70 grams) was added over a 1 hour period while maintaining the temperature at 110° C. The reaction mixture was heated to 110° C. for an additional hour at which time nuclear magnetic resonance spectra analysis showed that none of the starting N-phosphonomethyl-imino-diacetic acid remained. Assay of the reaction mixture (214.0 grams, 22.35% assay) showed that a 95.3% yield of N-phosphonomethyl glycine had been obtained.

EXAMPLE 6

N-Phosphonomethyl-imino-diacetic acid (20 grams) and concentrated hydrochloric acid (36.0 grams) were charged into a glass ampule and the ampule sealed. The ampule and contents were heated to 150° C. for 16 hours. The ampule was cooled, opened and the contents filtered through charcoal. The filtrate was evaporated to semi-dryness and then slurried with acetone (30 grams). The acetone slurry was filtered and the solid dried to yield 14 grams of a solid identified as N-phosphonomethyl glycine.

EXAMPLE 7

N-Phosphonomethyl-imino-diacetic acid (30 grams) and concentrated sulfuric acid (40 grams) were charged into a suitable reaction vessel. The mixture was heated at 100° to 110° C. for 1.5 hours. Water (40 ml.) was then added and the mixture heated to 100° C. The reaction mixture was cooled to 10° C. and neutralized with a 50% solution of sodium hydroxide in water to a pH of 1.5, a solid precipitated during neutralization. The mixture was then chilled and the solid removed by filtration and then dried to yield 25.1 grams of the solid which had a 47.9% assay of N-phosphonomethyl glycine.

EXAMPLE 8

A solution of 23.0 grams of N-phosphonomethyl-imino-diacetic acid in 40 grams of 75% sulfuric acid was heated at 145°–155° C. for 2 hours. Water and sodium hydroxide were added to adjust the pH to 1.8 and on standing N-phosphonomethyl glycine separated (15.7 grams, 43% assay).

EXAMPLE 9

A solution of N-phosphonomethyl-imino-diacetic acid in concentrated hydrochloric acid containing one equivalent of hydroiodic acid was heated at 150° C. for 8 hours in a sealed glass tube. Nuclear magnetic resonance analysis showed the presence of N-phosphonomethyl glycine, glycolic acid and acetic acid.

When the hydrochloric acid is omitted from the above experiment, N-phosphonomethyl glycine was produced.

EXAMPLE 10

A solution of N-phosphonomethyl-imino-diacetic acid in 47% hydrobromic acid was heated at 150° C. for 8 hours in a sealed glass tube. Nuclear magnetic resonance analysis showed the presence of N-phosphonomethyl glycine, glycolic acid and bromoacetic acid.

What is claimed is:

1. A process for the production of N-phosphonomethyl glycine which comprises forming an admixture consisting essentially of N-phosphonomethylimino diacetic acid and an acid selected from the group consisting of from 60% sulfuric acid to 20% fuming sulfuric acid, 47% hydrobromic acid, concentrated hydrochloric acid and hydriodic acid and heating said admixture to a temperature of from about 70° to about 200° C. whereby said N-phosphonomethylimino diacetic acid is decomposed to produce said N-phosphonomethyl glycine.

2. The process of claim 1 wherein the temperature is from 80° to 150° C.

3. The process of claim 1 wherein the acid is hydrobromic acid.

4. The process of claim 1 wherein the acid is sulfuric acid.

5. The process of claim 1 wherein the N-phosphonomethylimino diacetic acid is present in amounts of from 1 to 3 parts by weight and the acid is present in amounts of from 100 to 1 parts by weight.

6. The process of claim 5 wherein the acid is hydrobromic acid.

7. The process of claim 5 wherein the acid is hydrochloric acid.

8. The process of claim 6 wherein the temperature is from 80° to 150° C.

9. The process of claim 5 wherein the acid is sulfuric acid.

10. A process for the production of N-phosphonomethyl glycine which comprises forming an admixture consisting essentially of N-phosphonomethylimino diacetic acid and from 60% sulfuric aid to 20% fuming sulfuric acid and heating said admixture to a temperature of from about 70° to about 200° C. whereby said N-phosphonomethyl-imino diacetic acid is decomposed to produce said N-phosphonomethylglycine.

11. The process of claim 10 wherein the temperature is from 80° to 150° C.

12. The process of claim 10 wherein said fuming sulfuric acid contains from 1 to 2% sulfuric trioxide.

13. The process of claim 12 wherein said fuming sulfuric acid contains from 2 to 8% sulfur trioxide.

14. The process of claim 12 wherein the temperature is from 80° to 150° C.

* * * * *